(12) United States Patent
Sewell

(10) Patent No.: US 11,501,501 B1
(45) Date of Patent: Nov. 15, 2022

(54) BIOMETRIC FEEDBACK SYSTEM

(71) Applicant: Michael William Sewell, Louisville, KY (US)

(72) Inventor: Michael William Sewell, Louisville, KY (US)

(73) Assignee: Gresham Smith, Nashville, TN (US)

( * ) Notice: Subject to any disclaimer, the term of this patent is extended or adjusted under 35 U.S.C. 154(b) by 0 days.

(21) Appl. No.: 17/202,671

(22) Filed: Mar. 16, 2021

Related U.S. Application Data

(60) Provisional application No. 63/044,563, filed on Jun. 26, 2020.

(51) Int. Cl.

| | |
|---|---|
| *G06T 19/00* | (2011.01) |
| *A61B 5/16* | (2006.01) |
| *A61B 5/11* | (2006.01) |
| *A61B 5/00* | (2006.01) |
| *G06T 15/10* | (2011.01) |
| *G16H 50/30* | (2018.01) |
| *G16H 40/67* | (2018.01) |
| *A61B 5/0205* | (2006.01) |
| *A61B 5/024* | (2006.01) |

(52) U.S. Cl.
CPC .......... *G06T 19/006* (2013.01); *A61B 5/0205* (2013.01); *A61B 5/1112* (2013.01); *A61B 5/163* (2017.08); *A61B 5/165* (2013.01); *A61B 5/7445* (2013.01); *G06T 15/10* (2013.01); *G16H 40/67* (2018.01); *G16H 50/30* (2018.01); *A61B 5/02405* (2013.01)

(58) Field of Classification Search
CPC ....... G06T 19/006; G06T 15/10; A61B 5/163; A61B 5/0205; A61B 5/1112; A61B 5/165; A61B 5/7445; A61B 5/02405; G16H 40/67; G16H 50/30; G16H 50/00–50/80; G04G 21/00–21/025; G08B 21/00–21/0211
See application file for complete search history.

(56) References Cited

U.S. PATENT DOCUMENTS

| | | | |
|---|---|---|---|
| 6,599,243 B2 | 7/2003 | Woltermann et al. | |
| 6,968,294 B2 | 11/2005 | Gutta et al. | |
| 7,450,986 B2 | 11/2008 | Nguyen et al. | |
| 7,830,249 B2 | 11/2010 | Dorneich et al. | |
| 7,880,607 B2 | 2/2011 | Olson et al. | |
| 8,157,730 B2 | 4/2012 | LeBoeuf et al. | |
| 8,180,591 B2 | 5/2012 | Yuen et al. | |
| 8,738,321 B2 | 5/2014 | Yuen et al. | |
| 8,961,415 B2 | 2/2015 | LeBoeuf et al. | |
| 9,519,755 B2 * | 12/2016 | Saalasti | G16H 50/20 |
| 9,968,264 B2 | 5/2018 | Tzvieli et al. | |
| 10,055,121 B2 | 8/2018 | Chaudri et al. | |
| 10,076,250 B2 | 9/2018 | Tzvieli et al. | |
| 10,136,856 B2 | 11/2018 | Tzvieli et al. | |
| 10,534,900 B2 * | 1/2020 | Cheong | H04W 4/00 |
| 10,578,456 B2 | 3/2020 | Huang | |
| 10,595,730 B2 | 3/2020 | LeBoeuf et al. | |

(Continued)

*Primary Examiner* — Jonathan T Kuo
(74) *Attorney, Agent, or Firm* — Spencer Fane LLP; Steven J. Laureanti

(57) ABSTRACT

Biometric feedback systems and methods for measuring user reaction to the indoor or outdoor environment are described. In some embodiments, one or more user(s) wears a body-worn sensor and the user's heart rate variability or other indication of stress is monitored as the user travels along a pre-determined route.

16 Claims, 5 Drawing Sheets

(56) References Cited

U.S. PATENT DOCUMENTS

| | | | |
|---|---|---|---|
| 10,610,109 B2 | 4/2020 | Zhou | |
| 10,791,924 B2* | 10/2020 | Toth | A61B 5/1128 |
| 10,867,218 B2* | 12/2020 | Gallagher | G06K 9/6293 |
| 10,902,714 B2 | 1/2021 | Bergman et al. | |
| 11,030,885 B2 | 6/2021 | Kime et al. | |
| 11,156,464 B2* | 10/2021 | Young | G01S 19/13 |
| 2006/0065277 A1 | 3/2006 | Jung et al. | |
| 2010/0217099 A1* | 8/2010 | Le | A61B 5/4812 |
| | | | 600/301 |
| 2014/0288448 A1* | 9/2014 | Saalasti | G16H 40/63 |
| | | | 600/508 |
| 2015/0335288 A1 | 11/2015 | Toth et al. | |
| 2017/0011210 A1* | 1/2017 | Cheong | H04W 4/00 |
| 2017/0173262 A1 | 6/2017 | Veltz | |
| 2017/0231490 A1* | 8/2017 | Toth | A61B 5/1075 |
| | | | 600/558 |
| 2017/0360299 A1 | 12/2017 | Gelissen et al. | |
| 2018/0011978 A1 | 1/2018 | Reeckmann | |
| 2019/0025062 A1* | 1/2019 | Young | G01C 21/206 |
| 2019/0332902 A1* | 10/2019 | Gallagher | G06K 9/6293 |
| 2020/0305791 A1 | 10/2020 | Wirth et al. | |
| 2021/0034959 A1 | 2/2021 | Wood et al. | |
| 2021/0038088 A1 | 2/2021 | Atallah et al. | |

\* cited by examiner

BIOMETRIC FEEDBACK SYSTEM

RELATED APPLICATIONS

This application claims priority under 35 USC 119 to U.S. Application No. 63/044,563, filed Jun. 26, 2020, the contents of which are incorporated by reference in their entirety.

BACKGROUND

Technical Field

The present application relates to a system for measuring environmental stress, including autonomic stress to, for example, aid in the design and re-design process of any environment, including architectural settings, public spaces and landscapes.

BACKGROUND OF THE INVENTION

In the design and re-design of buildings, roads, parks and other features of the environment, community surveys, public forums and vehicle crash and other data are often consulted in the design and re-design process. However, data gained from such perspectives may be biased. For example, public forums may be dominated by a few participants, and survey results can be skewed by survey design. Moreover, participants may not be able to articulate or even be aware of subtle causes of stress in the environment. Thus, there is a need for a more objective measure for providing input in the design and re-design process.

Wearables for detecting heart rate and other biometrics are widely used in tracking individual heart rate, calories burned and other variables while users are exercising.

U.S. Patent Publication 2017/0360299 describes a wearable device that takes into account the geolocation of the user to provide a more accurate representation of calories burned. U.S. Patent Publication 2017/0360299 notes that a user in a higher-stress-level environment might be burning more calories simply by virtue of being in a crowded or potentially dangerous area (e.g., the user might need to periodically check if a car or train is coming so that he/she is not hit). However, the objective of U.S. Patent Publication 2017/0360299 is not to measure environmental stress; rather the goal of U.S. Patent Publication 2017/0360299 is to provide a more accurate representation of calories burned. Further, the aforementioned patent application does not pool data from a plurality of research subjects and display the information along with location data (e.g., on a map) to provide feedback on the environment. The aforementioned patent application also does not translate a user's biometric data into metrics that describe the user's emotional state (e.g., stress), tie that emotional state to a specific time and location, or infer relationships between the stress levels and the conditions of the built environment.

BRIEF DESCRIPTIONS OF THE DRAWINGS

Figure 4:
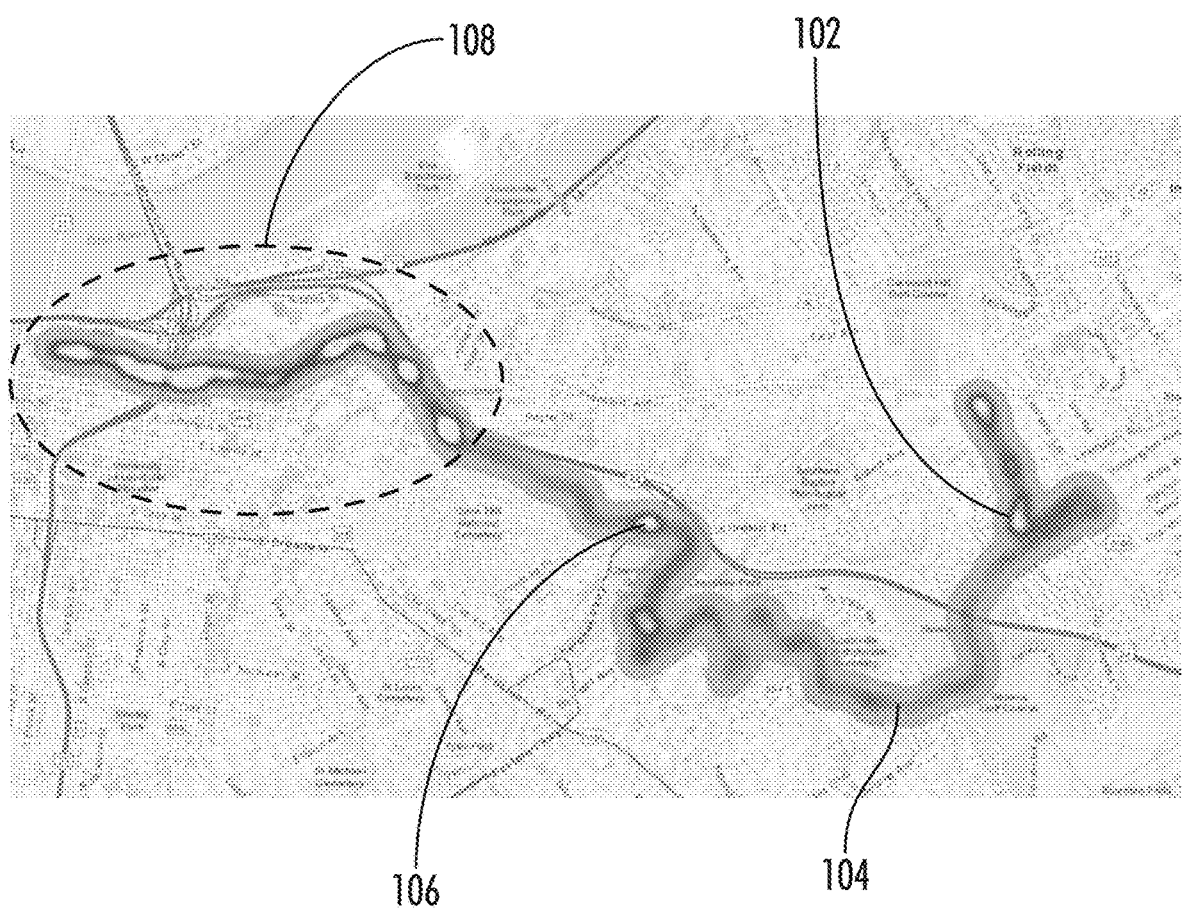
FIG. 4 is an illustration of a heat map in which a bicycle rider's stress score was calculated as the rider traveled along the indicated route.
Figure 5:
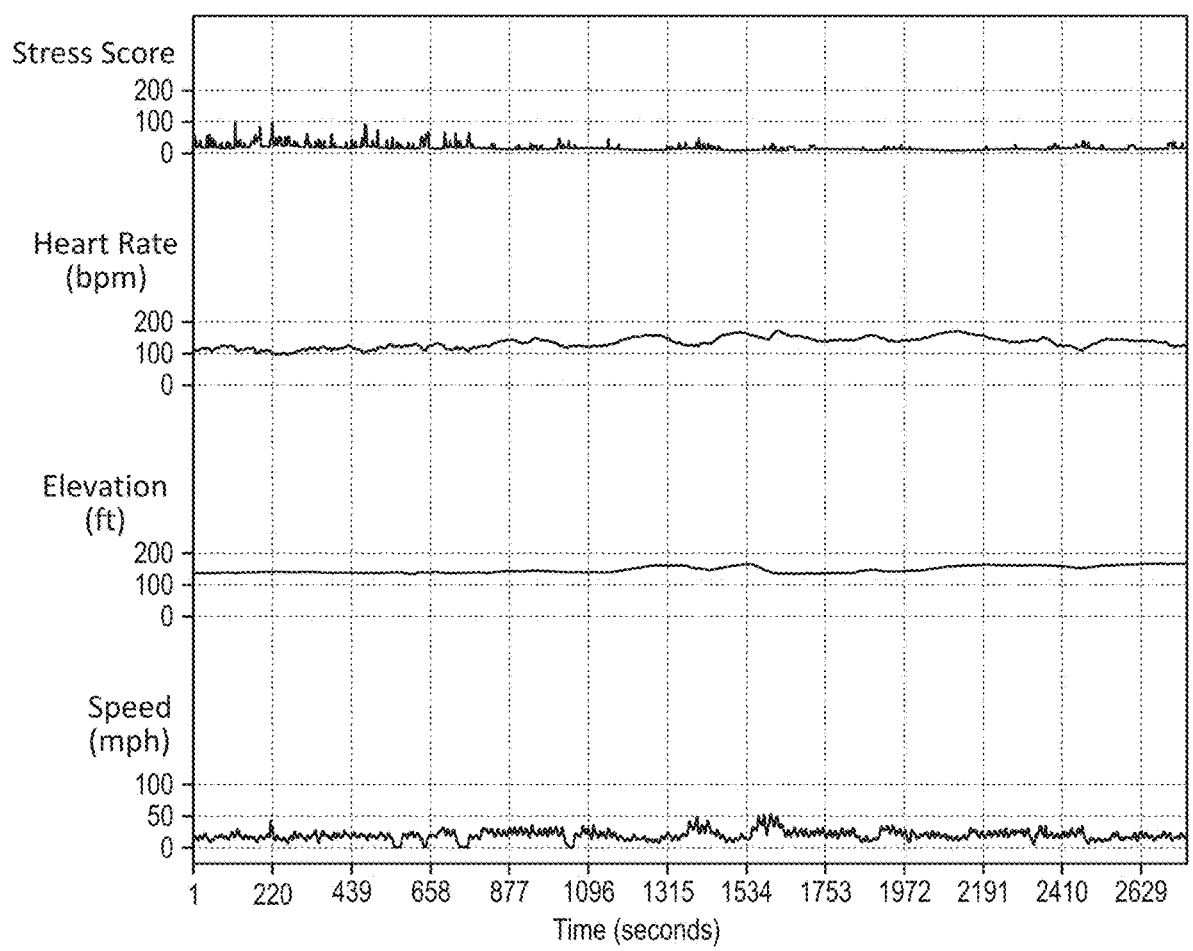

FIG. 5 provides four charts showing stress score, heart rate, elevation and speed as the bicycle rider traveled along the route shown in FIG. 4.

Figure 6:
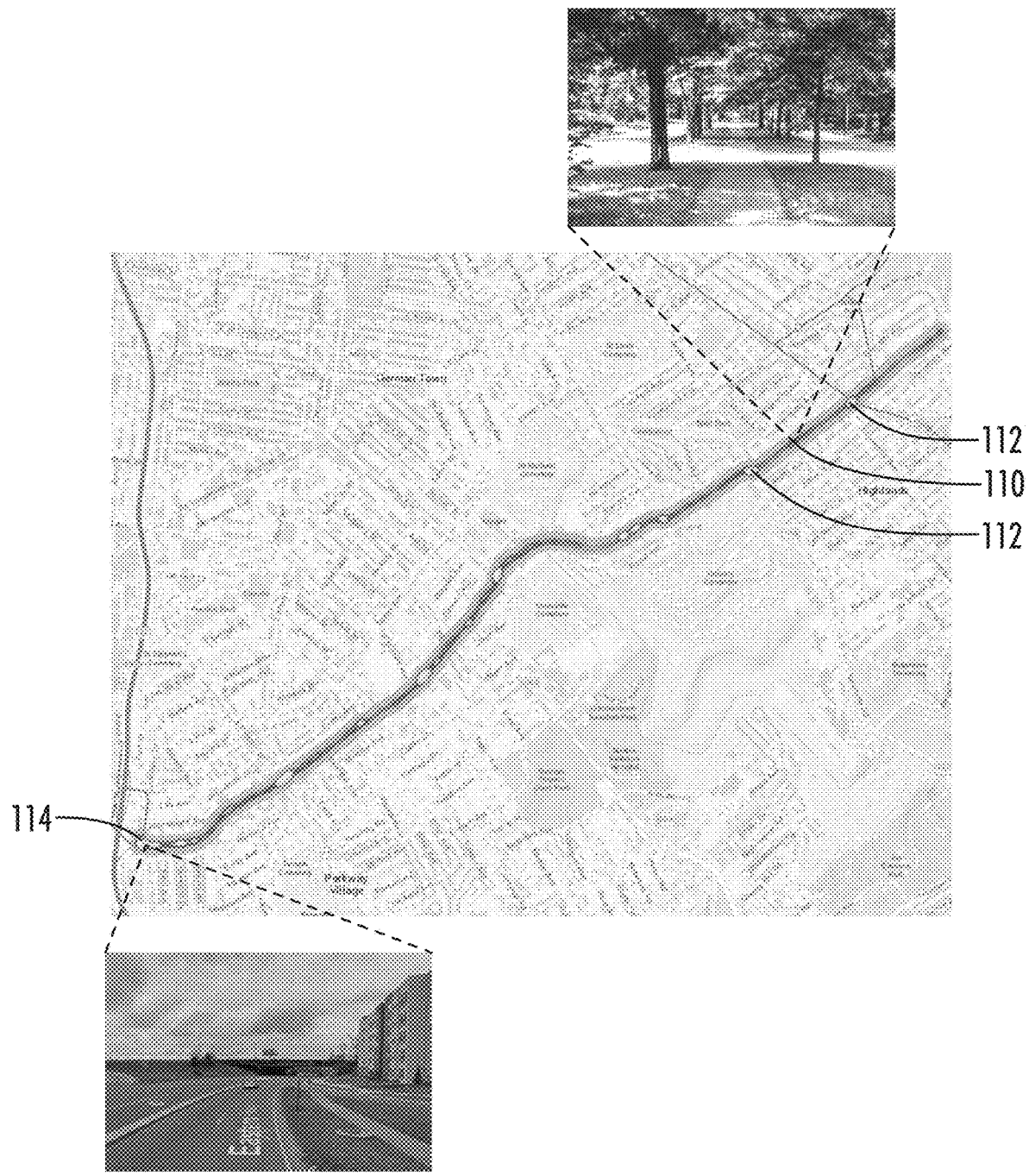

FIG. 6 is an illustration of a heat map in which walkers' stress scores are calculated as the walkers traveled along the indicated route.

BRIEF SUMMARY

What is Claimed is:

In some embodiments, the present disclosure provides a method of ascertaining biometric stress to an environmental condition comprising: a) using a plurality of biometric sensors (e.g., at least one sensor worn by each subject) to collect biometric data (e.g., heart rate, heart rate variability, blood pressure, oxygenation, galvanic response, facial sentiment analysis, and/or eye movement) over time from a plurality of subjects while the subjects move about a plurality of locations; b) using a plurality of location sensors to track the locations of the plurality of subjects over time while the subjects move about the plurality of locations, at least some of said subjects moving about at least partially overlapping locations (e.g, coming within five feet of the same location so that each location has readings from more than one subject); and c) grouping/segregating/sorting the biometric data, with or without filtering the data, by location (e.g., to assign a biometric score to each location).

Optionally, said biometric data comprises heart rate data of the respective subjects over time. Optionally, the method further comprises the step of filtering out physically-induced stress (so that the system only measures autonomic stress for each location). Optionally, said step of filtering out physically-induced stress occurs prior to grouping/segregating/sorting the biometric data by location. Optionally, the biometric data collected in step a) comprises the heart rate data of the respective subjects over time and wherein the method further comprises applying an algorithm to the biometric data to calculate heart rate variability over time for the respective subjects (e.g., by calculating the baseline heart rate of each respective subject within the plurality of subjects and applying the root mean square of the successive differences to the biometric data). Optionally, step c) further comprises displaying the biometric data segregated/sorted by location on an electronic screen (e.g., a computer screen). Optionally, step c) further comprises displaying the biometric data segregated/sorted by location and a map on an electronic screen. The system may be used in an outdoor or indoor environment. Thus, the term "map" as used herein includes, for example, reference maps as well as floorplans.

Optionally, the method further comprises the step of filtering the biometric data (e.g., to remove occasions where the user was standing still or the sensor fell off the subject). Optionally, the biometric data comprises data about one or more of heart rate, heart rate variability, blood pressure, oxygenation, galvanic response, facial sentiment analysis, and/or eye movement, etc. Optionally, the biometric sensor and the location sensor are located on a wearable (e.g., watch or other wrist strap, arm band, chest strap, etc.). Optionally, the method further comprises the step of d) assigning a biometric stress score to each of the plurality of locations. Optionally, the biometric sensor comprises a chest strap, arm band, watch or other wrist strap or other wearable configured to measure the subjects' heart rates. Optionally, the location sensor is a GPS tracker, indoor positioning system, or a device that employs other location based techniques. Optionally, the method further comprises using one or more power sources (e.g., a battery) to power the location sensor and the biometric sensor and the location sensor and biometric sensor are electronic. Optionally, the method further comprises the step of d) altering the environment at a location (e.g., adding trees, a sidewalk, adding width to a street, modifying architectural details, installing art, rearranging furniture, or changing lighting in response to a high stress reading). Optionally, the plurality of biometric sensors comprise a plurality of heart rate monitors.

In some cases, the plurality of biometric sensors and the plurality of location sensors may be located in different devices. Optionally, these different devices also record temporal data along with the biometric data or location data. The temporal data may be used to group/associate the biometric data with the corresponding location data at the same time interval. For example, a GPS unit may record a subject's location at time 1, and a wearable device worn by a user may record the subjects heart rate at time 1. The biometric data and location data may be merged, and the location at time 1 and the heart rate at time 1 may be grouped together.

In still further embodiments, the present disclosure provides a method of assigning autonomic stress to a location comprising: a) using a plurality of heart rate monitors to collect heart rate data from a plurality of subjects over time while the subjects move about a plurality of locations, each subject wearing a heart rate monitor; b) using a plurality of location sensors to track the location of the plurality of subjects over time while the subjects move about the plurality of locations, at least some of said subjects at least partially overlapping locations; c) applying an algorithm to the heart rate data for each subject to determine heart rate variability for each subject; and d) grouping/segregating/sorting heart rate variability by location. Optionally, the method further comprises displaying said heart rate variability for each location on an electronic screen. Optionally, the method further comprises displaying said heart rate variability for each location together with a map on an electronic screen.

In still further embodiments, the present disclosure provides a method of assigning autonomic stress to a location comprising: a) using a plurality of heart rate monitors to collect heart rate data from a plurality of subjects over time while the subjects move about a plurality of locations, each subject wearing a heart rate monitor; b) using a plurality of location sensors to track the location of the plurality of subjects over time while the subjects move about the plurality of locations, at least some of said subjects at least partially overlapping locations; c) filtering out physically-induced stress in the heart rate data, said step of filtering out physically-induced stress comprising calculating each subject's baseline heart rate and applying an algorithm comprising root mean square of the successive differences to the heart rate data; and d) grouping/segregating/sorting the filtered heart rate data by location.

Optionally, the method further comprises: e) after step d), displaying on an electronic screen autonomic stress levels for each of the plurality of locations.

In still further embodiments, the present disclosure provides a method of assigning autonomic stress to a location comprising: a) using a plurality of heart rate monitors to collect heart rate data from a plurality of subjects over time while the subjects move about a plurality of locations, each subject wearing a heart rate monitor; b) using a plurality of location sensors to track the location of the plurality of subjects over time while the subjects move about the plurality of locations, at least some of said subjects move about at least partially overlapping locations; c) grouping/segregating/sorting the heart rate data based on location and filtering out physically-induced stress from the heart rate data, said step of filtering out physically-induced stress comprising calculating each subject's heart rate variability and applying an algorithm comprising root mean square of the successive differences to the heart rate data; and d) displaying on an electronic display screen autonomic stress levels for the plurality of locations based, at least in part, on step c).

In still further embodiments, the present disclosure provides a method of assigning a biometric stress score to a location comprising: a) using at least one biometric sensor and at least one location sensor to simultaneously collect biometric data and location data for at least one subject over time as the at least one subject moves about a plurality of locations; and b) using the biometric data and the location data, with or without filtering the biometric data, to assign a biometric stress score to some or all of the plurality of locations.

Optionally, in step b), the biometric data is filtered to remove physical-induced stress. Optionally, the method further comprises the step of displaying the biometric stress scores on an electronic screen (e.g., optionally with a map).

In still further embodiments, the present disclosure provides a method of assigning autonomic stress to a location comprising: a) using a plurality of heart rate monitors and a plurality of location sensors to simultaneously collect heart rate data and location data for a plurality of subjects over time as the plurality of subjects move about a plurality of locations, each subject wearing a heart rate monitor; b) processing the heart rate data and the location data of each subject to assign a biometric stress score to some or all of the plurality of locations for each subject; and c) for each location, combining (e.g., averaging with or without removing outliers) the subject-level biometric stress scores to determine a cumulative biometric stress score for each location.

Optionally, the method further comprises the step of displaying the cumulative biometric stress scores on an electronic screen (e.g., optionally with a map). Optionally, step b) comprises applying an algorithm comprising root mean square of the successive differences to the heart rate data to filter out physically-induced stress.

In still further embodiments, the present disclosure provides a method of ascertaining biometric stress to an environmental condition comprising: a) presenting images of different locations or interactive 3D models on an electronic display to one or more subjects through virtual or augmented reality over time (e.g., through a head-mounted display worn by the subjects); b) using a plurality of biometric sensors to collect biometric data (e.g., heart rate, heart rate variability, blood pressure, oxygenation, galvanic response, facial sentiment analysis, and/or eye movement) over time from the one or more subjects while the subjects are presented the images; and c) grouping/segregating/sorting the biometric data, with or without filtering the data, by location (e.g., to assign a biometric score to each presented location).

DETAILED DESCRIPTION

Stress has been proven to be correlated with health issues, poor decision making and environmental avoidance. Quantifying the emotional responses and stressors we encounter as a result of the built environments around us could potentially help pave the way to better designs that encourage people to engage and enjoy the built environment.

To measure these stressors and responses, the inventor of the present application prototyped a platform that records the body's response to the built or natural environment and helps to quantify and interpret emotional responses in order to inform more empathic design solutions.

The working hypothesis was as follows: In theory, it may be possible to interpret certain types of human emotion by analyzing biomarkers such as heart rate, oxygenation, blood pressure, galvanic response, etc. These types of data points are becoming more and more readily accessible through wearable biometric sensor technologies—especially those integrated into smart watches. When combined with location data (for example, GPS, indoor positioning systems or location determined by other techniques), it may be possible to model the emotional reverberance of a specific place or a specific journey, providing designers with a valuable new research/feedback tool.

The autonomic response: In emotionally stressful situations, our bodies (specifically our Sympathetic Nervous Systems) automatically accelerate the production of adrenaline, leading to an immediate and involuntary increase in blood and oxygen flows to the brain and muscles. This is called an autonomic response, a form of emotional stress, which is different (and measurably distinguishable) from physical stress. For our purposes, we are focused on autonomic (emotional) stress (not physical stress) and how factors in the built environment can impact autonomic responses. Although there are autonomic emotional states that may be described as either good stress (known as eustress—e.g, the thrill of competition) or bad stress (known as distress—e.g., the sense of inability to control stimuli in one's environment), we are assuming for our studies in the context of placemaking, that eustress and distress are both generally undesirable, and that the preferred state is one of homeostasis.

Figure 2:
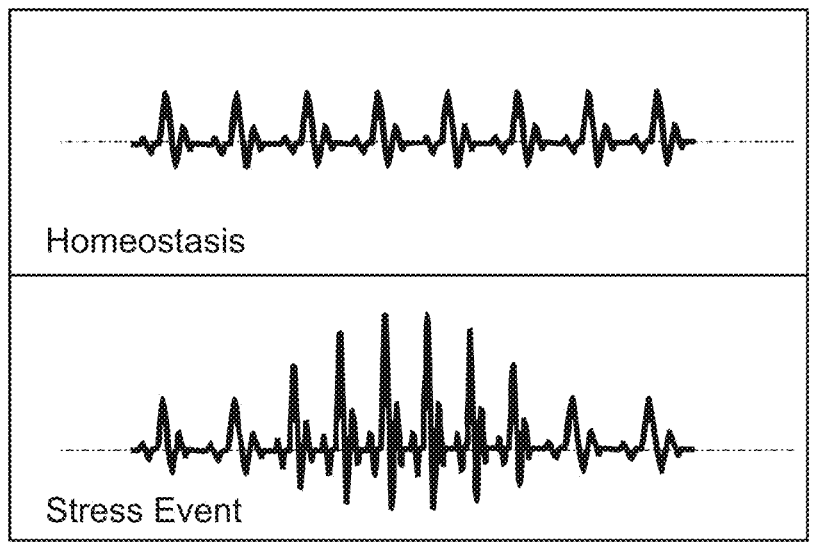
FIG. 2 is an illustration of heart rate variability of an exemplary subject when in homeostasis (upper chart) and when subjected to a stress event (lower chart).

The presence or absence of autonomic stress can be detected and measured by analyzing heart rate data. Most consumer grade fitness sensors are able to capture heart rate data (measured in beats per minute) over a period of time. In the instant application, it is desirable to isolate emotionally-induced stress by filtering out physically-induced stress. This may be done by calculating the individual's baseline heart rate, and applying a mathematical analytical algorithm called the Root Mean Square of the Successive Differences (RMSSD). The result (referred to as heart rate variability or HRV) is an estimation of autonomic stress, as shown in the exemplary charts included in FIG. 2 where the upper chart is homeostasis and the lower chart is a stress event.

Figure 3:
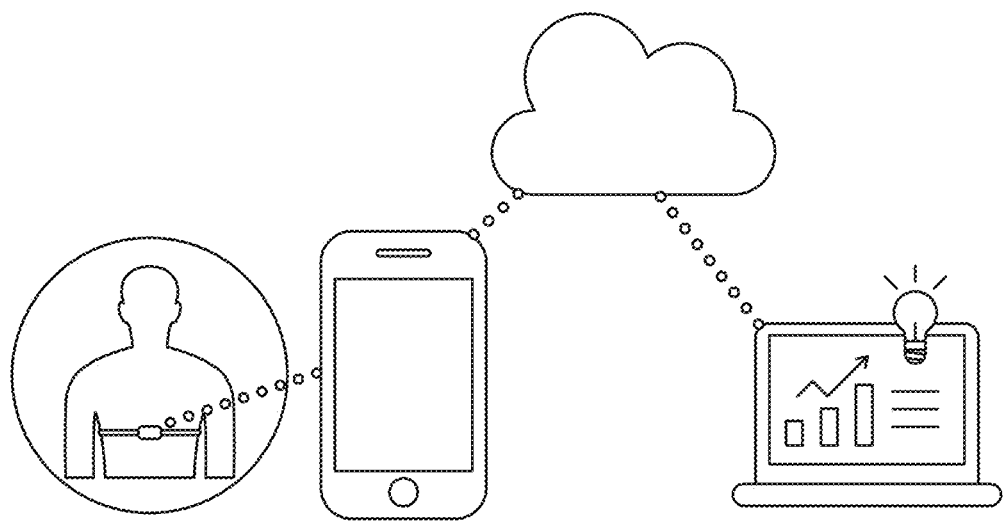
FIG. 3 is a schematic illustration of a computer and monitor system that may be used with a biometric feedback system of the present invention.

With this theory in mind, the present inventor's team used several different existing technologies to create a prototype workflow. The team set up digital linkages to move the heart rate data from the chest strap sensors to the fitness app on a smart phone and then to the fitness app's cloud server, as shown in the schematic illustration of FIG. 3. The team was then able to access the data from the fitness app's cloud via an API. The algorithms developed to interpret the cardio data were based on industry standards, including the RMSSD algorithm, to estimate induced stress at specific locations. These values are then normalized to provide a "Stress Score" on a linear scale relative to the RMSSD output. If the study involves multiple users/subjects (i.e., a sample size greater than 1), the "Stress Score" can also be compared across multiple users/subjects and further averaged to better identify outliers for specific users/subjects and establish broader patterns of stress for a larger userbase. In other words, if the study involves several users/research subjects and locations A and B, the Stress Scores for each user at the same location can be averaged (with or without removing outliers) to develop an average user Stress Score for location A and an average user Stress Score for location B.

The team debugged the platform by using data logged by a staff member on his daily bicycle commutes to and from the office. The heat map visualization of the commute route shown in FIG. 4 highlights locations of elevated autonomic stress where elevated stress is shown in lighter shading. Many of these locations are at street intersections requiring negotiations with vehicles, which happened more frequently near the city center. More interestingly, "hot spots" emerged that coincided with the memories of a repaired pothole and an accident along otherwise relatively calm stretches of the commute. For example, at location 102 the location of a former pothole still created stress even after the pothole was repaired. The lowest stress was recorded at location 104 where there is an abundance of green space and a lack of conflicts. At location 106, the memory of a collision with a car six months ago still creates a successful event at the location of the accident. In the city center, location 108, the stress levels are higher even though the terrain is flatter because the environment is not very user-friendly.

The stress charts in FIG. 5 appear to confirm that the inventor's measurements of stress do not correlate to physical exertion stressors. The Stress chart is the result of the RMSSD analysis of the heart rate data. Elevation ascents seem to show some correlation to increases in heart rate while descents correlate to increases in speed. However, the autonomic stress metrics in these locations seem relatively stable which points to successful measurements of autonomic stress based on the context at that location after removal of stress attributable to physical exertion. Conversely, the early stages of the route (in the city center) are on relatively flat terrain but show the highest amounts of autonomic stress. Also, the highest heart rates—all recorded in the second half of the commute—correlate to the lowest autonomic stress levels. Thus, it was observed that the inventor platform was successfully isolating emotional (autonomic) stress from physical stress. The horizontal axis in the charts below refers to time (in seconds from start). In the top graph, the vertical axis refers to the stress score (the stress score being a normalized value provided on a scale of 0-100 of the measurement of the stress response). In the heart rate chart, the vertical axis refers to heart rate in beats per minute. In the elevation chart, the vertical axis refers to elevation above sea level in feet. In the speed chart, the vertical axis refers to speed in miles per hour.

The system was then further applied to redesign of the Eastern Parkway in Louisville, Ky. There were a number of pre-design strategies employed to collect information and data, including: 1) an online survey which gathered information from the public about their opinions and impressions of the Parkway; 2) a town-hall-style public forum in which the community could interact with the design team about the Parkway; 3) a walking workshop tour of the Parkway with about 20 members of the group, in which they were able to record answers on iPad surveys at specific points along the Parkway walk; and 4) analysis of various types of third-party data, for example, vehicle crash data.

During the "walking workshop" on the Parkway, a small number of users wore chest straps to capture their heart rate data. The heat map shown in FIG. 6 indicated lower stress levels associated with locations where: 1) the sidewalks are further away from the street, or shielded from the street with natural vegetation; and 2) there are heavier tree canopies with mature trees. Conversely, higher stress was associated with locations where: 1) the sidewalks are closer to the street; and 2) there were highly active street intersections and the crossing durations were longer. More particularly, at location 110, some of the lowest levels of stress were located in the areas with abundant landscaping and good separation from vehicles. A favorite section of the parkway is bounded by very stressful access points 112 where it is necessary to cross traffic to get to the sidewalk in the median. The western terminus 114 of the Parkway merges with a major thoroughfare, with minimal consideration given to pedestrian experience, resulting in very high stress levels.

The stress data appeared to be well-aligned with the other datasets that were collected. Correlation with the crash data was especially interesting, seeing that locations of the highest crash counts coincided with some of the highest recorded stress levels, even in the absence of any actual crash events during the workshop.

In conclusion, it appears the method for deriving autonomic stress from heart rate variability data provided a useful tool to assess the level of latent stress in a physical environment. The method allows us to map which ambient settings cause stress; we can begin to quantify settings that lead to lower stress and homeostasis. The analysis provided us with quantifiable data for phenomena that have only been qualifiable up to this point.

A hypothetical example of a subject/user using the method follows. The subject begins by recording location and heart rate as the subject moves around outdoor or indoors. The subject walks, bikes, or rides in a car around town or in public space. Alternatively, the subject may move about an indoor space, such as a building. The subjects, for example, may feed the data to the software platform or alternatively the software platform may, for example, automatically retrieve the data. The platform may remove outliers (any bad data where the heart rate monitor may disconnect from the user). The platform may remove duplicate location data (optional, but used where a subject stands still at a certain location for an extended amount of time and forgets to pause his/her recording). The platform may convert the heart rate to heart rate variability. The platform may normalize and average readings across multiple subjects (if multiple subjects are present). The platform may export location data coupled with a stress score which can be plotted on, for example, a map.

Thus, the system described herein may be used to assign autonomic stress to locations by tracking movement of one or more subjects wearing a biometric sensor configured to measure biometric data and a location tracker (e.g, GPS tracker, indoor positioning system or other location based techniques) configured to track subject location. The biometric sensor may be used to measure one or more of heart rate, heart rate variability, blood pressure, oxygenation, galvanic response, facial sentiment analysis, etc. In the illustrated embodiment, subject heart rate variability was targeted using an algorithm comprising root mean square of the successive differences. In particular, it is believed that sharp increases or decreases in heart rate variability (HRV) are indicative of stress and a stable HRV is indicative of comfort, and thus, the object may be to improve HRV by altering the environment. To increase accuracy, a number of subjects (i.e., a large sample size) may be used and the biometrics of the subjects may be pooled. It will be appreciated that the subjects may not follow the exact same path so the method may consider locations within, for example, five feet of the same location.

Figure 1:
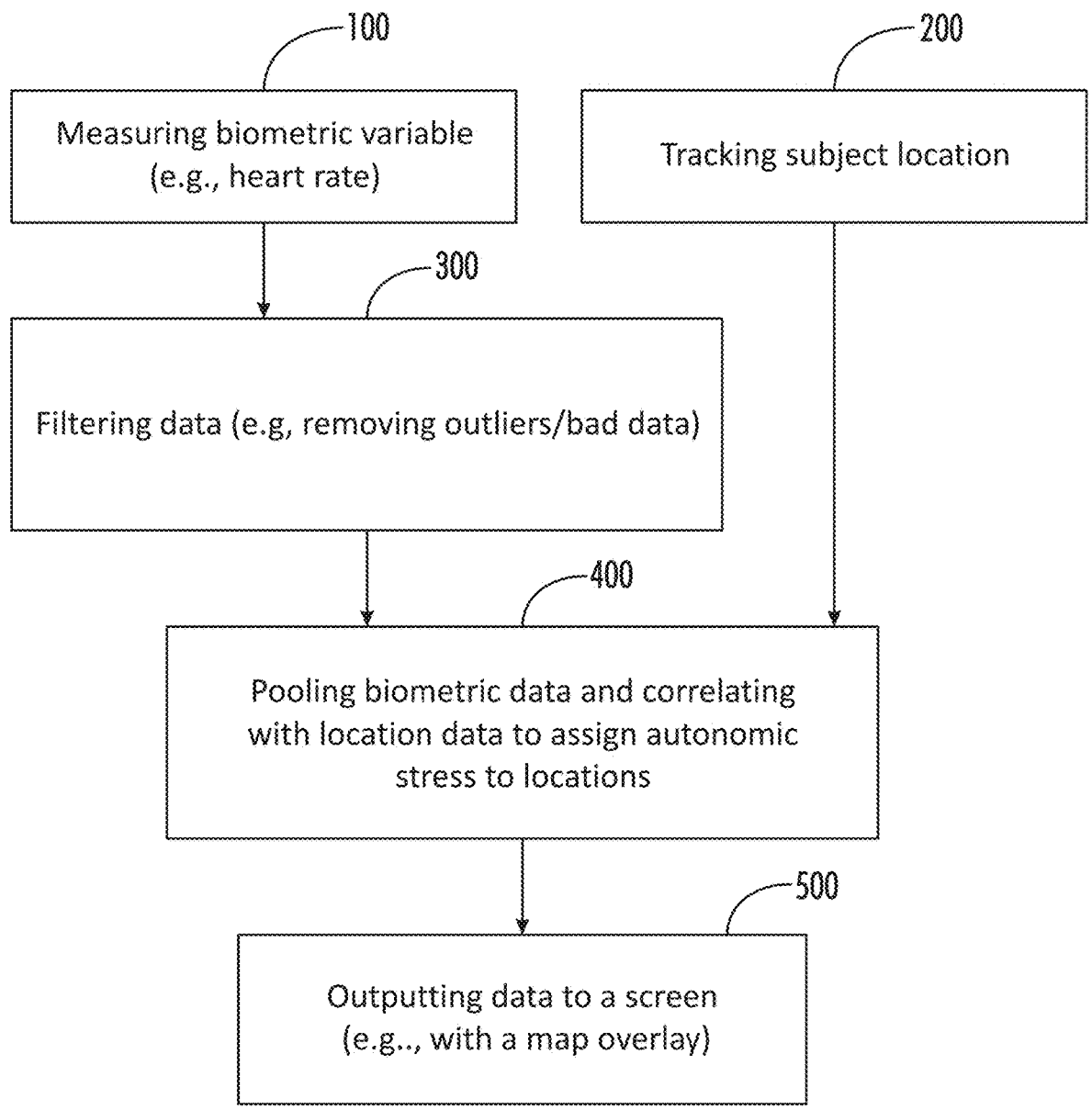
FIG. 1 shows a flow chart of an exemplary method of use of the biometric feedback system of the present invention.

It will also be appreciated that the location-correlated, biometric measurements developed through the system described herein may not be used in isolation but instead may be used to augment other information development techniques (e.g, surveys, interviews, observation, traffic data, etc.) in the design and re-design process. In other words, the biometric measurements may be used to augment known or later-developed techniques. A flow diagram illustrating exemplary operation of the method is included in FIG. 1 with steps 100, 200, 300, 400 and 500 as indicated.

It will be understood that the above method may be implemented through, for example, a software program running on a smart phone, laptop or other mobile computer.

The above methods could be modified to account for a survey in which the users do not physically walk around a place but instead are presented images in virtual or augmented reality. It will be appreciated that virtual and augmented reality are well known in the art and may include, for example, a head-mounted display, a processor, etc.

Those skilled in the art will understand how to make changes and modifications to the disclosed embodiments to meet their specific requirements or conditions. Changes and modifications may be made without departing from the scope and spirit of the invention. It is understood that use of the singular embraces the plural and vice versa. In addition, the steps of any method described herein may be performed in any suitable order and steps may be performed simultaneously if needed.

Terms of degree such as "generally", "substantially", "about" and "approximately" as used herein mean a reasonable amount of deviation of the modified term such that the end result is not significantly changed. For example, these terms can be construed as including a deviation of at least 5% of the modified term if this deviation would not negate the meaning of the word it modifies. In addition, the steps of the methods described herein can be performed in any suitable order, including simultaneously.

What is claimed is:

1. A method of ascertaining autonomic stress relative to a location comprising:
    a) using a plurality of biometric sensors to ascertain autonomic stress over time from a plurality of subjects while the plurality of subjects move about a plurality of locations;
    b) using a plurality of location sensors to track the locations of the plurality of subjects over time while the plurality of subjects move about the plurality of locations, at least some of said subjects at least partially overlapping locations;
    c) generating and displaying a heat map which indicates elevated autonomic stress by shading to depict the autonomic stress by geographic location along a particular route to correlate at least some of the plurality of locations with an autonomic stress level, wherein the shading is graphically depicted as continuous and non-gradated along the particular route; and
    d) physically altering the environment at one or more of the geographic locations, wherein each subject is wearing a respective biometric sensor and a respective location sensor during steps a) and b.

2. The method of claim 1 wherein the plurality of subjects move about the same path of travel during steps a) and b).

3. The method of claim 1 wherein said autonomic stress is ascertained by collecting heart rate and/or heart rate variability data from the plurality of subjects.

4. The method of claim 1 wherein the autonomic stress is ascertained by collecting heart rate data from the plurality of subjects and filtering out physically-induced stress, said step of filtering out physically-induced stress comprising calculating each subject's baseline heart rate and applying an algorithm to the heart rates that identifies an autonomic response.

5. The method of claim 1 wherein step c) further comprises displaying the autonomic stress grouped by geographic location on an electronic screen.

6. The method of claim 1 wherein the plurality of subjects move about the same path of travel and further wherein step c) further comprises displaying the autonomic stress grouped by location and a geographic map of the locations on an electronic screen.

7. The method of claim 1 wherein the biometric sensors only collect one type of information.

8. The method of claim 1 wherein the biometric sensors only collect heart rate data or heart rate variability.

9. The method of claim 1 wherein, in step a), the plurality of subjects move about an indoor area.

10. The method of claim 1, in step a), the plurality of subjects move about an outdoor geographic location, and further wherein the location sensors comprise GPS trackers.

11. The method of claim 1 further comprising using one or more power sources to power the location sensors and the biometric sensors and further wherein the location sensors and biometric sensors are electronic.

12. The method of claim 1 wherein the biometric sensors and the location sensors are located in different devices, the different devices also recording temporal data, and further wherein, in step c), the temporal data are used to group the autonomic stress with the corresponding geographic location.

13. A method of assigning autonomic stress to a location comprising:
   a) using a plurality of heart rate monitors to collect heart rate data from a plurality of subjects over time while the plurality of subjects move about a travel path, each subject wearing a heart rate monitor;
   b) using a plurality of location sensors to track the location of the plurality of subjects over time while the plurality of subjects move about the travel path;
   c) grouping the heart rate data based on location and filtering out physically-induced stress from the heart rate data, said step of filtering out physically-induced stress comprising calculating each subject's heart rate variability and applying an algorithm to the heart rate data;
   d) displaying on an electronic screen a heat map which indicates elevated autonomic stress by shading to depict autonomic stress levels for a plurality of geographic locations along the travel path based, at least in part, on step c), wherein the shading is graphically depicted as continuous and non-gradated along the travel path; and
   e) physically altering the environment at one or more of the geographic locations having an autonomic stress level, wherein each subject is wearing a respective heart rate monitor and a respective location sensor during steps a) and b).

14. The method of claim 13 wherein step d) comprises displaying on the electronic screen a map comprising i) the travel path and ii) the autonomic stress levels for a plurality of geographic locations along the travel path.

15. The method of claim 13 wherein the autonomic stress levels further incorporate crash data for the plurality of geographic locations.

16. The method of claim 15 wherein one or more the plurality of geographic locations of step d) comprises a roadway intersection.

* * * * *